US011178875B2

(12) United States Patent
Beery et al.

(10) Patent No.: US 11,178,875 B2
(45) Date of Patent: Nov. 23, 2021

(54) METHODS AND COMPOSITIONS FOR SPRAY DRYING GRAM-NEGATIVE BACTERIA

(71) Applicant: AgBiome, Inc., Research Triangle Park, NC (US)

(72) Inventors: Kyle Beery, Raleigh, NC (US); Alexander P. Schlesinger, Raleigh, NC (US); James D. Sievert, Morrisville, NC (US); Kelly S. Smith, Durham, NC (US)

(73) Assignee: AgBiome, Inc., Durham, NC (US)

( * ) Notice: Subject to any disclaimer, the term of this patent is extended or adjusted under 35 U.S.C. 154(b) by 0 days.

(21) Appl. No.: 16/307,109

(22) PCT Filed: Jun. 23, 2017

(86) PCT No.: PCT/US2017/039093
§ 371 (c)(1),
(2) Date: Dec. 4, 2018

(87) PCT Pub. No.: WO2017/223501
PCT Pub. Date: Dec. 28, 2017

(65) Prior Publication Data
US 2019/0223448 A1 Jul. 25, 2019

Related U.S. Application Data

(60) Provisional application No. 62/354,462, filed on Jun. 24, 2016, provisional application No. 62/354,424, filed on Jun. 24, 2016, provisional application No. 62/354,392, filed on Jun. 24, 2016.

(51) Int. Cl.
*A01N 63/02* (2006.01)
*A01N 25/12* (2006.01)
*C12N 1/04* (2006.01)
*A01N 25/00* (2006.01)
*A01N 63/27* (2020.01)

(52) U.S. Cl.
CPC ........... *A01N 63/27* (2020.01); *A01N 25/006* (2013.01); *A01N 25/12* (2013.01); *C12N 1/04* (2013.01)

(58) Field of Classification Search
CPC ...... A01N 63/00; A01N 25/006; A01N 63/10; A01N 25/12; C12N 1/04
See application file for complete search history.

(56) References Cited

U.S. PATENT DOCUMENTS

| 6,010,725 | A | 1/2000 | Meister et al. |
| 6,689,357 | B2 | 2/2004 | Casida, Jr. et al. |
| 8,119,172 | B2 | 2/2012 | Schatzmayr et al. |
| 9,540,608 | B2 * | 1/2017 | Pruitt ................. C02F 3/348 |
| 9,635,861 | B2 * | 5/2017 | Hammer ................. C12R 1/39 |
| 9,668,485 | B2 * | 6/2017 | Hammer ................. C12R 1/39 |
| 9,675,081 | B2 * | 6/2017 | Hammer ................. C12R 1/39 |
| 9,686,998 | B2 * | 6/2017 | Hammer ................. C12R 1/39 |
| 9,795,144 | B2 * | 10/2017 | Hammer ................. C12R 1/39 |
| 9,795,145 | B2 * | 10/2017 | Hammer ................. C12R 1/39 |
| 9,795,146 | B2 * | 10/2017 | Hammer ................. C12R 1/39 |
| 9,877,486 | B2 * | 1/2018 | Hammer ................. C12R 1/39 |
| 10,278,397 | B2 * | 5/2019 | Hammer ................. C12R 1/39 |
| 10,334,855 | B2 * | 7/2019 | Hammer ............... A01N 43/40 |
| 10,508,280 | B2 * | 12/2019 | Hammer ................. C12R 1/39 |
| 2003/0138936 | A1 | 7/2003 | Mizuguchi et al. |
| 2009/0142303 | A1 | 6/2009 | Edwards et al. |
| 2011/0045079 | A1 | 2/2011 | Edwards |
| 2013/0022580 | A1 * | 1/2013 | Pressi ................. A61K 36/898 424/93.7 |
| 2015/0327557 | A1 | 11/2015 | Hammer et al. |

FOREIGN PATENT DOCUMENTS

| CN | 101063120 | * | 5/2010 |
| WO | 2007022053 A2 | | 2/2007 |

OTHER PUBLICATIONS

Amiet-Charpentier et al., Microencapsulation of rhizobacteria by spray-drying: formulation and survival studies; Journal of Microencapsulation, vol. 15, No. 5; Sep. 27, 2008; pp. 639-659.
Morgan et al., Preservation of micro-organisms by drying; A review; Journal of Microbiological Methods, vol. 66, No. 2; Aug. 1, 2006; pp. 183-193.
Janning, et al., Development, production and certification of microbiological reference materials; Fresenius' Journal of Analytical Chemistry, vol. 352, No. 1-2; Jan. 1, 1995; pp. 240-245.
Janning, et al., Susceptibility of bacterial strains to desiccation: a simple method to test their stability in microbiological reference materials, Analytical Chimica Acta, vol. 286, No. 3; Feb. 28, 1994; pp. 469-476.

(Continued)

*Primary Examiner* — Mina Haghighatian
(74) *Attorney, Agent, or Firm* — Womble Bond Dickinson (US) LLP

(57) ABSTRACT

Methods for spray drying gram negative bacteria are provided. Such spray drying methods are performed under conditions that allow for the spray dried composition to retain the biological activity of interest of the gram-negative bacteria. Further provided are compositions comprising a spray dried gram-negative bacteria, where the spray dried formulation comprises at least $10^5$ CFU/gram of said gram-negative bacteria. The gram-negative bacteria employed in the various methods and compositions can comprise a biological activity of interest which, in specific embodiments, controls one or more pathogens that cause plant disease and/or improve at least one agronomic trait of interest. The spray dried formulation can be used as an inoculant for plants. Methods for growing a plant susceptible to plant disease and methods and compositions for controlling plant disease are also provided. Further provided are methods and compositions of increasing disease resistance in plants. Methods and compositions for improving plant health and/or improving at least one agronomic trait of interest are also provided.

11 Claims, No Drawings

(56) References Cited

OTHER PUBLICATIONS

International Search Report and Written Opinion for PCT/US2017/039093 dated Sep. 20, 2017.

Campos et al., "Microencapsulation by spray drying of nitrogen-fixing bacteria associated with lupin nodules," World J Microbiol Biotechnol, 2014, 30:2371-2378.

Pispan et al., "Comparison of cell survival rates of *E. coli* K12 and L acidophilus undergoing spray drying," Food and Bioproducts Processing, 2013, 91:362-369.

Yu et al., "Microencapsulation of Grain-Negative Bacteria by Spray Drying," International Journal of Food Engineering, 2010, 6(2):Article 3, 15 pp.

\* cited by examiner

METHODS AND COMPOSITIONS FOR SPRAY DRYING GRAM-NEGATIVE BACTERIA

CROSS REFERENCE TO RELATED APPLICATION

This application is a U.S. National Phase entry of International Patent Application No. PCT/US2017/039093 filed Jun. 23, 2017, which claims the benefit of U.S. Provisional Application Ser. No. 62/354,462, filed Jun. 24, 2016; U.S. Provisional Application Ser. No. 62/354,424, filed Jun. 24, 2016; and U.S. Provisional Application Ser. No. 62/354,392, filed Jun. 24, 2016, all of which are herein incorporated in their entireties by this reference.

FIELD OF THE INVENTION

The invention is drawn to methods and compositions for formulating bacteria.

SUMMARY

Methods for spray drying gram negative bacteria are provided. Such spray drying methods are performed under conditions that allow for the spray dried composition to retain the biological activity of interest of the gram-negative bacteria. Further provided are compositions comprising a spray dried gram-negative bacteria, where the spray dried formulation comprises at least $10^5$ CFU/gram of said gram-negative bacteria.

The gram-negative bacteria employed in the various methods and compositions can comprise a biological activity of interest which, in specific embodiments, controls one or more pathogens that cause plant disease and/or improve at least one agronomic trait of interest. The spray dried formulation can be used as an inoculant for plants. Methods for growing a plant susceptible to plant disease and methods and compositions for controlling plant disease are also provided. Further provided are methods and compositions of increasing disease resistance in plants. Methods and compositions for improving plant health and/or improving at least one agronomic trait of interest are also provided.

DETAILED DESCRIPTION

I. Overview

Methods for spray drying gram-negative bacteria and compositions produced from such methods are provided. Spray drying involves forcing a suspension of particles, in this case gram-negative bacterial cells, through a high-pressure heated nozzle. This produces a powder with a fine particle size and a very low water content. The inventors have found that gram-negative bacterial cells, which are not known for heat or desiccation tolerance, survive spray drying despite being vegetative. Prior to spray drying, the suspension can also be mixed with a number of carriers to improve survival of the bacterial cells, including lactose, lignosulfonates, maltodextrin, and dextrose. The carriers can also be combined, generally as one of the sugars combined with the lignosulfonates. This improves the survival of the bacterial cells. The dried powder can be used to promote plant health, as discussed in further detail herein. Spray drying is beneficial as a formulation method for microbial biologics due to the ready availability of spray drying equipment for industrial production, but more importantly due to the characteristics of the powders that are produced. Good dispersibility and long shelf life are important improvements in formulating.

As used herein, a "spray dryer feed" is the composition comprising the gram-negative bacteria and other component that is run through the spray dryer. A "primary spray dried powder" comprises the product that is emitted from the spray dryer. A "final spray dried powder" comprises the final formulated product which comprises the primary spray dried powder with any additional products blended therein.

II. Gram Negative Bacteria

Various gram negative bacteria can be employed in the spray drying methods provided herein. Such gram negative bacteria include, but are not limited to, *Escherichia coli* (*E. coli*), *Salmonella*, *Shigella*, *Enterobacteriaceae*, *Pseudomonas*, *Moraxella*, *Helicobacter*, *Stenotrophomonas*, *Bdellovibrio*, acetic acid bacteria, *Legionella*, etc. Other notable groups of gram-negative bacteria include the cyanobacteria, spirochaetes, green sulfur, and green non-sulfur bacteria.

In one embodiment, the gram negative bacteria employed in the methods and compositions provide herein is a *Pseudomonas* bacteria, including, for example, *Pseudomonas chlororaphis*, or the *Pseudomonas chlororaphis* strain deposited as NRRL No. B-50897 or NRRL No. B-50999 or biologically active variants thereof.

AIP050999 was deposited with the Patent Depository of the National Center for Agricultural Utilization Research Agricultural Research Service, U.S. Department of Agriculture, 1815 North University Street, Peoria, Ill. 61604 U.S.A. on Jan. 23, 2015 and assigned NRRL No. B-50999.

AIP1620 was deposited with the Patent Depository of the National Center for Agricultural Utilization Research Agricultural Research Service, U.S. Department of Agriculture, 1815 North University Street, Peoria, Ill. 61604 U.S.A. on Jan. 31, 2014 and assigned NRRL No. B-50897.

Each of the deposits identified above will be maintained under the terms of the Budapest Treaty on the International Recognition of the Deposit of Microorganisms for the Purposes of Patent Procedure. Each deposit was made merely as a convenience for those of skill in the art and is not an admission that a deposit is required under 35 U.S.C. § 112.

Active variants of the various gram negative bacteria disclosed herein, including active variants of NRRL No. B-50897 and NRRL No. B-50999 can be employed in the various spray drying methods and compositions. Such variants will retain the ability to control one or more plant diseases (i.e., reduce disease severity and/or reduce disease development) and/or control one or more plant pathogens. In some embodiments, variants will retain the ability to control one or more fungal plant diseases and/or one or more fungal pathogens. In other embodiments, variants will retain the ability to control ASR.

In specific embodiments, the bacterial strain is compatible with a biocide. A biocide is a chemical substance which can exert a controlling effect on an organism by chemical or biological means. Biocides include pesticides, such as fungicides; herbicides; insecticides, other crop protection chemicals, and the like. Such compounds are discussed in detail elsewhere herein. A bacterial strain is compatible with a biocide when the bacterial strain is able to survive and/or reproduce in the presence of an effective amount of a biocide of interest. In instances where the bacterial strain is not compatible for a biocide of interest, if desired, methods can be undertaken to modify the bacterial strain to impart the compatibility of interest. Such methods to produce modified bacterial strains include both selection techniques and/or transformation techniques.

By "modified bacterial strain" is intended a population wherein the strain has been modified (by selection and/or transformation) to have one or more additional traits of interest. In some cases, the modified bacterial strain comprises any one of NRRL No. B-50897 and NRRL No. B-50999 or an active variant thereof. In specific embodiments, the modified bacterial strain is compatible with a biocide of interest, including but not limited to, resistance to an herbicide, fungicide, pesticide, or other crop protection chemical. The modified biocide-resistant strains have the same identification characteristics as the original sensitive strain except they are significantly more resistant to the particular herbicide, fungicide, pesticide, or other crop protection chemical. Their identification is readily possible by comparison with characteristics of the known sensitive strain. Thus, isolated populations of modified bacterial strains are provided.

An increase in resistance to a biocide (i.e., for example, a herbicide, fungicide, pesticide, or other crop protection chemical resistance) refers to the ability of an organism (i.e., bacterial cell or spore) to survive and reproduce following exposure to a dose of the biocide (e.g, herbicide, fungicide, pesticide, or other crop protection chemical) that would normally be lethal to the unmodified organism or would substantially reduce growth of the unmodified organism. In specific embodiments, the increase in resistance to a biocide is demonstrated in the presence of an agriculturally effective amount of the biocide.

In such instances, the modified gram-negative bacterial strain having resistance to one or more biocides is useful for enhancing the competitiveness of bacterial strains particularly over other microbial agents which are not resistant to herbicides, fungicides, pesticides, or other crop protection chemicals. Therefore, compositions provided herein include selected or engineered bacterial strains and modified populations of bacterial strains. These bacterial strains or modified gram-negative bacterial strains can be used as an inoculant for plants. They can also be applied as a spray application directly to the aerial parts of plants, and can be mixed with the herbicide or other chemical to which they have been modified to become tolerant.

Thus, active variants of the gram-negative bacterial strains disclosed herein, include for example, a modified strain, such that the active variant controls a plant disease and further are able to grow in the presence of at least one biocide.

Recombinant bacterial strains having resistance to an herbicide, fungicide, pesticide, or other crop protection chemical can be made through genetic engineering techniques and such engineered or recombinant bacterial strains grown to produce a modified population of bacterial strains. A recombinant bacterial strain is produced by introducing polynucleotides into the bacterial host cell by transformation. Methods for transforming microorganisms are known and available in the art. See, generally, Hanahan, D. (1983) Studies on transformation of *Escherichia coli* with plasmids *J. Mol. Biol.* 166, 557-77; Seidman, C. E. (1994) In: *Current Protocols in Molecular Biology*, Ausubel, F. M. et al. eds., John Wiley and Sons, NY; Choi et al. (2006) J. Microbiol. Methods 64:391-397; Wang et al. 2010. *J. Chem. Technol. Biotechnol.* 85:775-778. Transformation may occur by natural uptake of naked DNA by competent cells from their environment in the laboratory. Alternatively, cells can be made competent by exposure to divalent cations under cold conditions, by electroporation, by exposure to polyethylene glycol by treatment with fibrous nanoparticles, or other methods well known in the art.

Herbicide resistance genes for use in transforming a recombinant bacterial strain include, but are not limited to, fumonisin detoxification genes (U.S. Pat. No. 5,792,931); acetolactate synthase (ALS) mutants that lead to herbicide resistance, in particular the sulfonylurea-type herbicides, such as the S4 and/or Hra mutations; inhibitors of glutamine synthase such as phosphinothricin or basta (e.g., bar gene); and glyphosate resistance (EPSPS gene); gluphosinate, and HPPD resistance (WO 96/38576, U.S. Pat. Nos. 6,758,044; 7,250,561; 7,935,869; and 8,124,846), or other such genes known in the art. The disclosures of which are herein incorporated by reference. The bar gene encodes resistance to the herbicide basta, the nptII gene encodes resistance to the antibiotics kanamycin and geneticin, and the ALS-gene mutants encode resistance to the sulfonylurea herbicides including chlorsulfuron, metsulfuron, sulfometuron, nicosulfuron, rimsulfuron, flazasulfuron, sulfosulfuron, and triasulfuron, and the imadizolinone herbicides including imazethapyr, imazaquin, imazapyr, and imazamethabenz.

To identify and produce a modified population of bacterial strains through selection, the bacterial strains are grown in the presence of the herbicide, fungicide, pesticide, or other crop protection chemical as the selection pressure. Susceptible agents are killed while resistant agents survive to reproduce without competition. As the bacterial strains are grown in the presence of the herbicide, fungicide, pesticide, or other crop protection chemical, resistant bacterial strains successfully reproduce and become dominant in the population, becoming a modified population of bacterial strains. Methods for selecting resistant strains are known and include U.S. Pat. Nos. 4,306,027 and 4,094,097, herein incorporated by reference. The active variant of the bacterial strain comprising a modified population of bacterial strains will have the same identification characteristics as the original sensitive strain except they are significantly more tolerant to the particular herbicide, fungicide, pesticide, or other crop protection chemical. Thus, their identification is readily possible by comparison with characteristics of the known sensitive strain.

Further, active variants of the various bacterial strains provided herein can be identified employing, for example, methods to identify groups of derived and functionally identical or nearly identical strains include Multi-locus sequence typing (MLST), concatenated shared genes trees, Whole Genome Alignment (WGA), and Average Nucleotide Identity (ANI). Each will be considered below. While many are also useful for higher-level groupings (species and above), the cutoffs and methodology below will be focused on those appropriate for a fine level of resolution. One approach to increasing the resolution of the rRNA gene is to use multiple genes or loci, particularly those that change more rapidly but are still universally present. There are many techniques for identifying these genes and classifying new sequences in a previous framework (see, for example, Darling, A. E., et al., (2014) *PeerJ* 2:e243; Wu, M., et al., (2008) *Genome Biology* 9(10):R151; Wu, M., et al., (2012) *Bioinformatics* 28(7): 1033-34; Mende, D. R., et al., (2013) *Nature Methods* 10(9):881-84; Jolley, K. A., et al., (2010) *BMC Bioinformatics* 11(1):595; and Larsen, M. V., et al., (2012) *Journal of Clinical Microbiology* 50(4): 1355-61). The various references cited herein provide publicly available gene sets and either set cut off values or provide methods to determine the cut off that will provide the same cut off for the same group of organisms. The larger the number of genes, the more resolution is possible, but the lack of those genes in other species make them difficult to analyze in the same framework. Cutoffs to define a group will differ based on the number and specific genes used. One extension of MLST is to use all universally shared genes (therefore the maximum possible loci) for a group of strains for instance, as implemented in Benedict, M. N., et al., ((2014) *BMC Genomics* 15(1):8) in a concatenated shared gene alignment and inferred tree. WGA is a related series of method that aligns the entire genome sequence (not just genes or defined loci) between two or many organisms (see, for example, Angiuoli, S. V., et al., (2011) *Bioinformatics* 27(3):334-42; Darling, A. E., et al., (2010) *PLoS ONE* 5(6):e11147; and Treangen, T. J., et al., (2014) *Genome Biology* 15(11):524). For both MLST, concatenated shared gene trees, and WGA, methods exist to determine the distance between naturally occurring groups, given enough genetic information from related organism genomes (see, for example, Didelot, X., et al., (2007) *Genetics* 175(3): 1251-66; and Lang, P., et al., (2010) *Applied and Environmental Microbiology* 76(6):1913-25; and Bishop, C., et al. (2009) *BMC Biology* 7(1)1741-7007-7-3.). The exact cutoffs defining each taxonomic group in a single method may vary (for instance, from 95% for rapidly changing groups to 99.7% for more slowly changing groups (Bishop, C., et al. (2009) *BMC Biology* 7(1)1741-7007-7-3), but membership of a strain in a group is determinable using publicly available methods and will remain constant for that group. These naturally occurring groups indicate a group of closely related organisms that share an ecological function (Koeppel, A., et al. (2008) *PNAS* 105(7): 2504-2509; and Cohan, F., et al. (2007) *Current Biology* 17(10): R373-86)—due to the nature of these groups, a skilled environmental microbiologist would predict that strains from the same group would be useful unless some specific change could be shown that would disrupt a particular function. Finally, ANI (see, for example, Konstantinidis, K. T., et al., (2005) *PNAS USA* 102(7):2567-72; and Richter, M., et al., (2009) *PNAS* 106 (45):19126-31) and variants (see, for example, Varghese, N. J., et al., *Nucleic Acids Research* (Jul. 6, 2015): gkv657) are based on summarizing the average nucleotides shared between the genomes of strains that align in WGAs. While methods may differ slightly, for one widely implemented ANI method a cutoff of 99% defines a functional group (see, for example, Konstantinidis, K. T., et al., (2005) *PNAS USA* 102(7):2567-72).

In another aspect, the active variants of the isolated bacterial strain(s) disclosed herein includes strain(s) that may be closely related to any of the above strains on the basis of 16S rDNA sequence identity. In an embodiment, the at least one strain is at least 95% identical to any of the above strains on the basis of 16S rDNA sequence identity, at least 96% identical to any of the above strains on the basis of 16S rDNA sequence identity, at least 97% identical to any of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity, at least 99.5% to any of the above strains on the basis of 16S rDNA sequence identity or at least 100% to any of the above strains on the basis of 16S rDNA sequence identity. Active variants of the bacteria identified by such methods may retain the ability to improve at least one agronomic trait when applied in an effective amount to a plant, plant part, or an area of cultivation, including for example, reducing plant disease severity and/or reducing plant disease development.

III. Spray Drying Process and Compositions Related to the Same

A. Biological Activity and Viability of the Primary Spray Dried Gram Negative Bacteria Powder and/or Final Spray Dried Gram Negative Bacteria Powder The gram-negative bacteria are spray dried under conditions that retain the viability of the gram negative bacteria and/or retain the biological activity of interest of the gram-negative bacteria both in the primary spray dried powder and in the final spray dried powder.

The viability of the gram-negative bacteria in the primary spray dried powder and/or in the final spray dried powder can be measured by determining the colony forming units (CFU) per gram of the spray dried composition. Such an amount can comprise a concentration of the bacterial strain of at least about $10^5$ CFU/gram to about $10^{11}$ CFU/gram, about $10^4$ CFU/gram to about $10^{11}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, about $10^{11}$ CFU/gram to about $10^{12}$ CFU/gram. In other embodiments, the concentration of the bacterial strain comprises at least about $10^4$ CFU/gram, at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram in the primary spray dried powder or in the final spray dried powder.

In specific embodiments, the spray dried gram negative bacteria remain viable over time at room temperature (21° C.) or at lower temperatures (such as 4° C. or lower). Following formulation, viability of the spray dried gram negative bacteria can be retained for a least about 1 month, 2 months, 3 months, 4 months, 5 months, 6 months, 7 months, 8 months, 9 months, 10 months, 11 months, 1 year, 1.5 years, 2 years, 2.5 years or more. Thus, in specific embodiments, the CFU/g of the spray dried formulated composition comprises a reduction of about less than 0.5 logs of CFU/g, of about less than 1 log of CFU/g, about less than 2 logs of CFU/gram, about less than 3 logs of CFU/g, about less than 4 logs of CFU/g from the time of spray dry manufacturing to at least about 1 month, 2 months, 3 months, 4 months, 5 months, 6 months, 7 months, 8 months, 9 months, 10 months, 11 months, 1 year, 1.5 years, 2 years, 2.5 years or more post spray dry manufacturing at room temperature (21° C.) or at lower temperature (such as 4° C. or lower). In specific embodiments, the CFU/g of the spray dried formulated composition comprises an about less than five-fold reduction of CFU/g, an about less than ten-fold reduction of CFU/g, an about less than 100-fold reduction of CFU/gram, an about less than 1000-fold reduction of CFU/g, an about less than 10,000-fold reduction of CFU/g from the time of spray dry manufacturing to at least about 1 month, 2 months, 3 months, 4 months, 5 months, 6 months, 7 months, 8 months, 9 months, 10 months, 11 months, 1 year, 1.5 years, 2 years, 2.5 years or more post spray dry manufacturing at room temperature (21° C.) or at lower temperature (such as 4° C. or lower).

In one embodiment, the biological activity of interest of the gram-negative bacteria controls disease-causing plant pathogens and/or improves at least one agronomic trait of interest and/or improves plant health. Such biological activity can be assayed by applying to a plant having a plant disease or at risk of developing a plant disease an effective amount of at least one of the primary spray dried powder comprising the gram negative bacteria or the final spray dried powder comprising the gram negative bacteria and determining if the spray dried bacteria composition controls a plant pathogen that causes the plant disease.

In specific embodiments, the biological activity of the gram-negative bacteria prevents or reduces plant disease caused by one or more plant pathogens. For example, the gram negative bacterial strains employed in the methods and compositions disclosed herein target one or more fungal pathogens that cause plant disease. For example, any of the bacterial strain provided herein or active variant thereof can have antifungal activity against one, two, three, four, five or more fungal pathogens and/or fungal diseases described herein.

The biological activity of the gram negative bacteria can control one or more fungal pathogens. A fungal pathogen can be, but is not limited to, a fungus selected from the group consisting of *Botrytis cinerea, Cersospora* spp, *Cercospora sojina, Cercospora beticola, Alternaria solani, Rhizoctonia solani, Blumeria graminis* f sp. *Tritici, Erysiphe necator, Podosphaera xanthii, Golovinomyces cichoracearum, Erysiphe lagerstroemiae, Sphaerotheca pannosa, Colletotrichum cereale, Apiognomonia errabunda, Apiognomonia veneta, Colletotrichum gloeosporiodes, Discula fraxinea, Plasmopara viticola, Pseudoperonospora cubensis, Peronospora belbahrii, Bremia lactucae, Peronospora lamii, Plasmopara obduscens, Pythium cryptoirregulare, Pythium aphanidermatum, Pythium irregulare, Pythium sylvaticum, Pythium myriotylum, Pythium ultimum, Phytophthora capsici, Phytophthora nicotianae, Phytophthora infestans, Phytophthora tropicalis, Phytophthora sojae, Fusarium graminearum, Fusarium solani, Fusarium oxysporum, Fusarium graminicola, Gibberella zeae, Colletotrichum graminicola, Phakopsora* sp., *Phakopsora meibomiae, Phakopsora pachyrizi, Puccinia triticina, Puccinia recondita, Puccinia striiformis, Puccinia graminis, Puccinia* spp., *Venturia inaequalis, Verticillium* spp, *Erwinia amylovora, Monilinia fructicola, Monilinia lax,* and *Monilinia fructigena.*

In some embodiments, the fungal pathogen is selected from the group consisting of *Botrytis cinerea, Cercospora sojina, Alternaria solani, Rhizoctonia solani, Erysiphe necator, Podosphaera xanthii, Colletotrichum cereal, Plasmopara viticola, Peronospora belbahrii, Pythium aphanidermatum, Pythium sylvaticum, Pythium myriotylum, Pythium ultimum, Phytophthora nicotianae, Phytophthora infestans, Phytophthora tropicalis, Phytophthora sojae, Fusarium graminearum, Fusarium solani, Phakopsora pachyrizi* and *Venturia inaequalis.*

In further embodiments, the fungal pathogen is *Phakopsora* sp., including *Phakopsora pachyrhizi* and/or *Phakopsora meibomiae.*

In specific embodiments, the gram negative bacterial strains can have biological activity that targets one or more insect or insect pests. The term "insects" or "insect pests" as used herein refers to insects and other similar pests such as, for example, those of the order Acari including, but not limited to, mites and ticks. Insect pests include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias erytheme, Corcyra cephalonica, Cydia latiferreanus, Cydia pomonella, Datana integerrima, Dendrolimus sibericus, Desmiafeneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails,* and *Yponomeuta padella.*

Insect pests also include insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, Coleoptera, etc., particularly Lepidoptera. Insect pests of the invention for the major crops include, but are not limited to: Maize: *Ostrinia nubilalis*, European corn borer; *Agrotis ipsilon*, black cutworm; *Helicoverpa zeae*, corn earworm; *Spodoptera frugiperda*, fall army worm; *Diatraea grandiosella*, southwestern corn borer; *Elasmopalpus lignosellus*, lesser cornstalk borer; *Diatraea* saccharalis, sugarcane borer; western corn rootworm, e.g., *Diabrotica virgifera virgifera*; northern corn rootworm, e.g., *Diabrotica longicornis barberi*; southern corn rootworm, e.g., *Diabrotica undecimpunctata howardi*; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcom maggot; *Agromyza parvicornis*, corn blotch leafminer; *Anaphothrips obscrurus*, grass *thrips; Solenopsis milesta*, thief ant; *Tetranychus urticae*, two spotted spider mite; Sorghum: *Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; chinch bug, e.g., *Blissus leucopterus leucopterus; Contarinia sorghicola*, sorghum midge; *Tetranychus cinnabarinus*, carmine spider mite; *Tetranychus urticae*, two-spotted spider mite; Wheat: Pseudaletia unipunctata, army worm; *Spodoptera frugiperda*, fall armyworm; *Elasmopalpus lignosellus*, lesser cornstalk borer; *Agrotis orthogonia*, pale western cutworm; *Elasmopalpus lignosellus*, lesser cornstalk borer; *Oulema melanopus*, cereal leaf beetle; *Hypera punctata*, clover leaf weevil; southern corn rootworm, e.g., *Diabrotica undecimpunctata howardi*; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco *thrips; Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; boll weevil, e.g., *Anthonomus grandis; Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion *thrips; Franklinkiella fusca*, tobacco *thrips; Tetranychus cinnabarinus*, carmine spider mite; *Tetranychus urticae*, two-spotted spider mite; Rice: *Diatraea* saccharalis, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhoper; chinch bug, e.g., *Blissus leucopterus leucopterus; Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet army worm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean *thrips; Thrips tabaci*, onion *thrips; Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus; Acrosternum hilare*, green stink bug; *Euschistus servus*, brown stink bug; *Jylemya platura*, seedcom maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufimanus, Meligethes nigrescens, Meligethes canadianus*, and *Meligethes viridescens*; Potato: *Leptinotarsa decemlineata*, and Colorado potato beetle.

The methods and compositions provided herein can also be used against Hemiptera such as *Lygus hesperus, Lygus lineolaris, Lygus pratensis, Lygus rugulipennis Popp, Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster*, Coreidae, Pyrrhocoridae, Tinidae, Blostomatidae, Reduviidae, and Cimicidae. Pests of interest also include *Araecerus fasciculatus*, coffee bean weevil; *Acanthoscelides obtectus*, bean weevil; *Bruchus rufmanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple curculio; *Sternechus paludatus*, bean stalk weevil; *Hypera brunnipennis*, Egyptian alfalfa weevil; *Sitophilus* granaries, granary weevil; *Craponius inaequalis*, grape curculio; *Sitophilus zeamais*, maize weevil; *Conotrachelus nenuphar*, plum curculio; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; *Tribolium castaneum*, red flour beetle; *Tenebrio molitor*, yellow mealworm.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The primary spray dried powder comprising a gram negative bacteria or a final spray dried powder can be tested for pesticidal activity against insects by assaying insects in early developmental stages, e.g., as larvae or other immature forms. The insects may be reared in total darkness at from about 20 degree C. to about 30 degree C. and from about 30% to about 70% relative humidity. Bioassays may be performed as described in Czapla and Lang (1990) *J. Econ. Entomol.* 83 (6): 2480-2485. Methods of rearing insect larvae and performing bioassays are well known to one of ordinary skill in the art.

B. Spray Dryer Feed Comprising Gram Negative Bacteria

Generally, the spray drying process comprises forming a spray dryer feed. A "spray dryer feed" comprises the gram-negative bacteria and other components that is run through the spray dryer.

In specific embodiments, the spray dryer feed comprises gram-negative bacteria and an effective amount of glycerol. An effective amount of glycerol is such as to sufficiently decrease the viscosity of the cell paste and/or to act as a protectant for the gram negative cells during the spray drying process. As used herein, a "cell paste" comprises a population of cells that has been centrifuged and/or filtered or otherwise concentrated. When forming a spray dryer feed, a given percentage of a component within the spray dryer feed is based on the assumption that the cell paste contains between about 10% and 25% dry solids. In some embodiments, additional solids can be added to the dry solid cell paste to obtain a spray dryer feed comprising about 15% to about 40% dry solids. The amount of glycerol added to the cell paste can be about 2%, 4%, 5%, 6%, 7%, 9%, 10%, 11%, 12%, 15%, 20%, 25% or more by weight (weight/ weight %) of the cell paste mixture (based on the assumption that the cell paste will contain about 10% to about 25% dry solids). In specific embodiments, the amount of glycerol comprises about 3% to about 7% by weight (weight/weight %) of the cell paste mixture (based on the assumption that the cell paste will contain about 10% to about 25% dry solids), about 4% to about 6% by weight (weight/weight %) of the cell paste mixture (based on the assumption that the cell paste will contain about 10% to about 25% dry solids), about 3% to about 12% by weight (weight/weight %) of the cell paste mixture (based on the assumption that the cell paste will contain about 10% to about 25% dry solids), about 8% to about 12% by weight (weight/weight %) of the cell paste mixture (based on the assumption that the cell paste will contain about 10% to about 25% dry solids), about 9% to about 11% by weight (weight/weight %) of the cell paste mixture (based on the assumption that the cell paste will contain about 10% to about 25% dry solids), or about 5% to about 10% by weight (weight/weight %) of the cell paste mixture (based on the assumption that the cell paste will contain about 10% to about 25% dry solids).

In some embodiments, the viscosity of the spray dryer feed comprising the cell pellet/glycerol mixture can be sufficiently reduced to allow efficient spray drying through the addition of water. In specific embodiments, the water to cell/glycerol mixture ratio is about 1:1 or about 2:1 or about 3:1, or about 4:1 by weight (weight/weight %) of the cell pellet.

In other embodiments, the spray dryer feed comprises gram-negative bacteria and an effective amount of maltodextrin. An effective amount of maltodextrin is such as to enhance viability following spray drying and/or to act as a protectant for the gram negative cells during the spray drying process. When forming a spray dryer feed, a given percentage of a component within the spray dryer feed is based on the assumption that the cell paste contains about 10% to about 25% dry solids. In some embodiments, the spray dryer feed comprises about 10% to about 25%, about 11% to about 25%, about 12% to about 25%, about 13% to about 25%, about 14% to about 25%, about 15% to about 25%, about 16% to about 25%, about 17% to about 25%, about 18% to about 25%, about 19% to about 25%, about 20% to about 25%, about 21% to about 25%, about 22% to about 25%, about 23% to about 25%, or about 24% to about 25% dry solid cell paste. In other embodiments, the spray dryer feed comprises about 10% to about 15%, about 11% to about 15%, about 12% to about 15%, about 13% to about 15%, about 14% to about 15%, about 10% to about 20%, about 11% to about 20%, about 12% to about 20%, about 13% to about 20%, about 14% to about 20%, about 15% to about 20%, about 16% to about 20%, about 17% to about 20%, about 18% to about 20% or about 19% to about 20% dry solid cell paste. In other embodiments, the spray dryer feed comprises about 13% to about 24%, about 13% to about 23%, about 13% to about 22%, about 13% to about 21%, about 13% to about 20%, about 13% to about 19%, about 13% to about 18%, about 13% to about 17%, about 13% to about 16%, about 13% to about 15%, or about 13% to about 14% dry solid cell paste. The amount of maltodextrin added to the cell paste can be about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more by weight (weight/weight %) of the cell paste mixture (based on the assumption that the cell paste will contain about 10% to about 25% dry solids). In some embodiments, the amount of maltodextrin added to the cell paste is sufficient to obtain a spray dried feed comprising at least about 15% to about 40% dry solids (maltodextrin and dry solid cell paste). In some embodiments, the spray dried feed comprises about 15% to about 40% dry solids, about 15% to about 35% dry solids, about 15% to about 30% dry solids, about 15% to about 25% dry solids, about 15% to about 20% dry solids, about 20% to about 40% dry solids, about 20% to about 35% dry solids, about 20% to about 30% dry solids, about 20% to about 25% dry solids, about 25% to about 40% dry solids, about 25% to about 35% dry solids, about 25% to about 30% dry solids, about 30% to about 40% dry solids, about 30% to about 35% dry solids, about 30% to about 33% dry solids, about 31% to about 40% dry solids, about 32% to about 39% dry solids, about 33% to about 38% dry solids, about 34% to about 37% dry solids, about 35% to about 40% dry solids, about 36% to about 40% dry solids, about 37% to about 40% dry solids, or about 38% to about 40% dry solids.

In specific embodiments, the amount of maltodextrin comprises about 3% to about 7% by weight (weight/weight %) of the cell paste mixture (based on the assumption that the cell paste will contain about 10% to about 25% dry solids), about 4% to about 6% by weight (weight/weight %) of the cell paste mixture (based on the assumption that the cell paste will contain about 10% to about 25% dry solids), about 3% to about 12% by weight (weight/weight %) of the cell paste mixture (based on the assumption that the cell paste will contain 25% solids), about 8% to about 12% by weight (weight/weight %) of the cell paste mixture (based on the assumption that the cell paste will contain about 10% to about 25% dry solids), about 9% to about 11% by weight (weight/weight %) of the cell paste mixture (based on the assumption that the cell paste will contain 25% solids), by weight (weight/weight %) about 5% to about 10% of the cell paste mixture (based on the assumption that the cell paste will contain about 10% to about 25% dry solids), about 10% to about 20% of the cell paste mixture (based on the assumption that the cell paste will contain about 10% to about 25% dry solids), about 20% to about 30% of the cell paste mixture (based on the assumption that the cell paste will contain about 10% to about 25% dry solids) or about 30% to about 40% of the cell paste mixture (based on the assumption that the cell paste will contain about 10% to about 25% dry solids). In specific embodiments, when maltodextrin is added to the spray dryer feed, glycerol is not added to the feed.

In some embodiments, the viscosity of the spray dryer feed comprising the cell pellet/maltodextrin mixture can be sufficiently reduced to allow efficient spray drying through the addition of water. In specific embodiments, the water to cell/maltodextrin mixture ratio is about 1:1 or about 2:1 or about 3:1, or about 4:1 by weight (weight/weight %) of the cell pellet.

In other embodiments, additives that increase dispersability and/or wettability following spray drying are added. For example, dispersability and/or wettability following spray drying can be increased by adding sodium lignosulfonate at 5% by weight (weight/weight %) of the cell pellet. Alternatively, the sodium lignosulfonate can be added to the spray dryer feed comprising the cell pellet/glycerol mixture or the cell pellet/maltodextrin mixture at about 2% to 25% by weight (weight/weight %) of cell pellet, at about 2% to about 20% by weight (weight/weight %) of cell pellet, at about 2% to about 15% by weight (weight/weight %) of cell pellet, at about 2% to about 10% by weight (weight/weight %) of cell pellet, at about 2% to about 6% by weight (weight/weight %) of cell pellet, or at about 4% to about 6% by weight (weight/weight %) of the cell pellet. Non-limiting examples of sodium lignosulfonate include Marasperse AG, Polygon F, Polyfon T, Polyfon O, Polyfon H, Marasperse N-22, Vanisperse CB, Ultrazine NA, Ufoxane 3A, Borresperse NA, Borresperse 3A, and Kraftsperse EDF-450.

Additional carriers may be added to the spray dryer feed to enhance cell survival. These carriers are typically sugars or sugar derivatives, including lactose, maltodextrin, or corn starch. The amount of carrier added can vary but a typical amount is 5% by weight (weight/weight %) based on starting cell pellet weight. In other embodiments, the amount of carrier added is about 2% to about 20% in weight based on the weight of the starting cell pellet; about 2% to about 7% in weight based on the weight of the starting cell pellet; about 7% to about 10% in weight based on the weight of the starting cell pellet; about 10% to about 15% in weight based on the weight of the starting pellet; or about 15% to about 20% in weight based on the weight of the starting pellet.

In specific embodiments, an effective amount of one or more of a sugar or sugar derivatives, including lactose, maltodextrin, or corn starch and an effective amount of one or more of a sodium lignosulfonate is added to the cell pellet/glycerol mixture or to the cell pellet/maltodextrin mixture to form the spray dryer feed.

C. Primary Spray Dried Powder Comprising Gram Negative Bacteria

A "primary spray dried powder" comprises the product that is emitted from the spray dryer. In non-limiting embodiments, the spray dryer feed is fed into the spray dryer nozzle via a peristaltic pump. In other non-limiting embodiments, the spray dryer feed is fed into the spray dryer nozzle via a piston pump (single fluid nozzle), a progressive cavity pump (two-fluid nozzle) or a centrifugal pump (rotary nozzle). The primary spray dried powder is collected. Spray dryer parameters include pump speed, atomization pressure, inlet temperature, and aspirator air flow %. In specific embodiments, the inlet temperature is about 90 degrees C. to about 120 degrees C., about 120 degrees C. to about 200 degrees C. about 95 degrees C. to about 120 degree C., or about 120 degrees C. to about 150 degrees C.

Various types of nozzles can be used in the spray dry process. Each nozzle type will allow the spray dryer feed to be atomized or fluidized and will influence the size of the particle produced from the spray dried process. The size of a droplet produced from the spray drying process can vary and will depend on the type of nozzle and pressure employed. The particle size can range from about 10 microns to about 40 microns, from about 40 microns to about 50 microns, from about 50 microns to about 75 microns, from about 75 microns to about 100 microns, from about 100 microns to about 150 microns, from about 150 microns to about 200 microns, or from about 200 microns to about 250 microns. In specific embodiments, the particle size following spray drying is about 50 to 200 microns. In further embodiments, such particle size is produced using a two-fluid nozzle.

Such nozzles include, but are not limited to, a rotary disk nozzle, a two-fluid nozzle, or a single fluid nozzle. Generally, for rotary nozzles the pressure will be atmospheric pressure or slightly above atmospheric pressure.

For the two-fluid nozzle the pressure can range from about 100 psi to about 200 psi, from about 100 psi to about 150 psi, from about 150 psi to about 200 psi, from about 200 psi to about 300 psi, from about 200 psi to about 250 psi, from about 250 psi to about 300 psi, from about 300 psi to about 400 psi, from about 300 psi to about 350 psi, from about 350 psi to about 400 psi, from about 400 psi to about 500 psi from about 400 to about 450 psi, or from about 450 psi to about 500 psi.

For the single fluid nozzle, the pressure can range from about 1000 psi to about 5000 psi. In specific embodiments, the pressure range when employing a 1 fluid nozzle is about 1000 psi to about 1500 psi, about 1500 psi to about 2000 psi, about 2000 psi to about 2500 psi, about 2500 psi to about 3000 psi, about 3000 psi to about 3500 psi, about 3500 psi to about 4000 psi, about 4000 psi to about 4500 psi, or about 4500 psi to about 5000 psi.

In one non-limiting embodiment, the following spray dry settings are used when using a Buchi B-290 spray dryer: Atomization pressure (Q-flow): 35 mm Inlet temperature: 115 C; Aspirator air flow %: 100; feed flow rate: 9 ml/min. In light of these parameters, one of skill can determine equivalent parameters for other spray drying units which will allow for the production of the primary spray dried powder comprising the gram-negative bacteria.

Dryer residence time can vary during the spray drying process. In specific embodiments, the residence time in the tower is 6, 7, 8, 9, or 10 seconds. In other embodiments, the residence time in the tower can range from about 6 seconds to about 50 seconds, from about 6 seconds to about 7 seconds, from about 7 seconds to about 8 seconds, from about 8 seconds to about 10 seconds, from about 6 seconds to about 10 seconds, from about 10 seconds to about 20 seconds, from about 20 seconds to about 30 seconds, from about 30 seconds to about 40 seconds, or from about 40 seconds to about 50 seconds, or greater. Dryer residence times in a lab scale spray dryer can be about 1 second to about 5 seconds, while dryer residence times in a pilot spray dryer can be about 2 seconds to about 20 seconds.

If a cyclone is employed in the spray drying process, the residence time in the cyclone is about 4 seconds to about 20 seconds, about 4 seconds to about 15 seconds, about 4 seconds to about 10 seconds, about 4 seconds to about 8 seconds or about 6 seconds to about 9 seconds. In specific embodiments, when a rotary nozzle is employed, the residence time in the tower is about 6 seconds and the residence time in the cyclone is about 8 seconds.

In specific embodiments, a fluid bed can be used with a tower in combination with a bag house or cyclone. Residence time in the fluid bed can range from about 1 minute to about 30 minutes. In other embodiments, the time in the fluid bed can range from about 1 min to about 5 min, from about 5 min to about 10 min, from about 10 min to about 15 min, from about 15 min to about 20 min, from about 20 min to about 25 min, or from about 25 min to about 30 min.

The inlet and outlet temperature of the tower can be varied. In specific embodiments, the inlet temperature is about 110° C. to about 200° C. In one embodiment, the inlet temp is about 110° C. In other embodiments, the inlet temperature can be from about 80° C. to about 90° C., from about 90° C. to about 100° C., from about 100° C. to about 110° C., about 110° C. to about 120° C., from about 120° C. to about 130° C., from about 130° C. to about 140° C., from about 140° C. to about 150° C., from about 150° C. to about 160° C., from about 160° C. to about 170° C., from about 170° C. to about 180° C., from about 180° C. to about 190° C., or from about 190° C. to about 200° C.

The outlet temperature of the tower can be varied. In specific embodiments, the outlet temperature is from about 60° C. to about 100° C. In other embodiments, the outlet temperature is about 60° C. to about 80° C. In specific embodiments, the outlet temperature is about 40° C. to about 50° C., from about 50° C. to about 60° C., from about 60° C. to about 70° C., from about 70° C. to about 80° C., from about 80° C. to about 90° C. from about 90° C. to about 100° C., from about 100° C. to about 110° C., or from about 110° C. to about 120° C.

A non-limiting example of the spray drying process is as follows. A gram-negative bacteria, such as NRRL No. B-50897, is fermented and centrifuged to concentrate the broth to dry cell solids of about 17% as measured on a heated moisture balance. Cell concentrate batches are formulated in preparation for spray drying as follows. A feed slurry comprising the gram negative bacteria, such as NRRL No. B-50897, cell concentrate (~20% dry cell solids) and maltodextrin at 5-40%, 5-10%, 10-15%, 15%-20%, 20-25%, 25%-30%, 30%-35%, 35%-40%, or 40%-45% based on dry cell solids weight is prepared. No glycerol is added to the spray dry feed. The spray dry feed is fed into a commercial spray drying tower with a short residence time (6 s) and a two fluid nozzle to minimize shear on feed. A low pump feed and spray gas pressure (<500 psi) is employed. Inlet air temperature is about 150° C. and outlet temperature is about 80° C. or lower. The dried particle size is in the range of 50-200 µm. Immediate discharge of material from the cyclone away from heat or directly into fluidized bed dryer to further cool the product and/or agglomerate the spray dried powder particles occurs.

D. Final Spray Dried Powder Formulation Comprising Gram Negative Bacteria

A "final spray dried powder formulation" comprises the final formulated product which comprises the primary spray dried powder with any additional products blended therein. In specific embodiments, additional ingredients are blended into the spray dried powder until well mixed. This can include the remainder of the carrier if it was not all added during the spray drying process. Additional ingredients include flow aids such as calcium silicates at 1-10% by weight and additional dispersants. In one embodiment, the calcium silicate is MicroCel E. Non-limiting examples of additional ingredients include, but are not limited to, one or more of the following: sugars, including but not limited to, lactose, dextrose, sucrose, milk powders, whey protein, casein, maltodextrin; mineral carriers, including but not limited to, all types of clays (bentonite, montmorillonite, kaolin, hectorite etc.), silicas, diatomaceous earths, perlite, zeolite, carboxymethyl cellulose, starches (potato, rice, corn, tapioca, etc.), flours; protectants, including but not limited to, glycerol, sorbitol, xanthan gum, duitan gum, gum arabic, sodium alginate, gelatin, trehalose, fructo- and galacto-oligosaccharides, mannitol, dextran, yeast extract, dextrin, pectin; lignosulfonates, Polyvinyl pyrrolidone, alcohol ethoxylates, organosilicone surfactants, polyglycerol fatty esters, sorbitan fatty acid ethoxylates, siloxanes, acrylates, alkyl naphthalene sulfonate condensates, anionic comb polymers, block copolymer, diester sulfosuccinate, phosphate ester, tristyrylphenol ethoxylate, alkyl benzene sulfonates, castor oil ethoxylates, vegetable oils (ethoxylated and methylated varieties as well), sulfosuccinates, ethyl lactates, alkylamine ethoxylates, diester sulfosuccinates, dioctyl sodium sulfosuccinate, ethoxylated acetylenic diol, sodium lauryl sulfate, salts, proteins, peptides and amino acids.

In one embodiment, the primary spray dried powder comprising the gram-negative bacterial composition is blended with a flow aid. Non-limiting examples of flow aids include, but are not limited to, MicroCel E, Sipernate 22S, Sipernat 22, Sident 22S, Sipernat 50, Sipernat 50S, HI-SIL 233 Silica, and HI-SIL SAC Silica. In one embodiment, the flow aid is added to about 2%, 5%, 7%, 10%, 15%, 20%, 25% or more by weight of the final spray dried powdered formulation. In a specific embodiment, the flow aid is added to about 5% to about 10% by weight of the final spray dried powdered formulation.

In other embodiments, the primary spray dried powder comprising the gram-negative bacterial composition is blended with a surfactant. Non-limiting examples of surfactants include Silwet 408, Xiameter OFX-5211 Fluid, Q-5212 Super Wetting Agent, and Break-Thru S 200. In one embodiment, the surfactant is added to about 1%, 2%, 3%, 4%, 5%, 6%, 7%, 8%, 9%, 10%, or 15% or more by weight of the final spray dried powder formulation. In a specific embodiment, the flow aid is added to about 1% to about 5% by weight of the final spray dried powder formulation.

In other embodiments, the sodium lignosulfonate can be added to the primary spray dried powder comprising the gram-negative bacteria at about 1% to about 50%, about 1% to about 40%, about 1% to about 30%, about 1% to about 20%, about 1%6 to about 15%, about 1% to about 10%, about 1% to about 5%, about 5% to about 50%, about 5% to about 40%, about 5% to about 30%, about 5% to about 20%, about 5% to about 15%, about 5% to about 10%, about 10% to about 50%, about 10% to about 40%, about 10% to about 30%, about 10% to about 20%, about 10% to about 15% by weight of the final spray dried powder formulation. Non-limiting examples of sodium lignosulfonate include Marasperse AG, Polyfon F, Polyfon T, Polyfon O, Polyfon H, Marasperse N-22, Vanisperse CB, Ultrazine NA, Ufoxane 3A, Borresperse NA, Borresperse 3A, and Kraftsperse EDF-450.

In specific embodiments an effective amount of any combination of one or more of the flow aid, surfactant, and/or sodium lignosulfonate can be added to the primary spray dried powder comprising the gram-negative bacteria to form the final spray dried powder formulation.

Additional processing steps to form the final spray dried powder formulation can include milling to reduce particle size which can be accomplished, for example, by using an impact mill utilizing a defined size mesh screen or an air mill. Finally, a sieving step can be included if necessary to remove any oversized material. Typically, a 50- or 100-mesh screen is utilized for this purpose.

Non-limiting embodiments include:

1. A formulation comprising a spray dried gram-negative bacteria composition, wherein the spray dried gram-negative bacteria composition retains the biological activity of interest of the gram-negative bacteria and said spray dried formulation comprises at least $10^5$ CFU/gram of said gram-negative bacteria.

2. The formulation of embodiment 1, wherein said spray dried formulation comprises at least $10^5$ CFU/gram to about $10^{12}$ CFU/gram.

3. The formulation of embodiments 1 or 2, wherein said spray dried gram-negative bacteria composition comprises a non-polymeric and a non-oil formulation.

4. The formulations of any one of embodiment 1 or 2 or 3, wherein the viability of the gram-negative bacteria in the formulation does not reduce by more than 10 fold when stored for at least 1 month at 25 degree C.

5. The formulation of any one of embodiment 1-4, wherein the gram-negative bacteria is a *Pseudomonas*.

6. The formulation of embodiment 5, wherein the gram-negative bacteria was deposited as NRRL No. B-50897.

7. The formulation of any one of embodiment 1-6, wherein said formulation comprises a primary spray dried powder.

8. The formulation of any one of embodiment 1-6, wherein said formulation comprises a final spray dried powder.

9. A method for producing a spray dried formulation comprising a gram-negative bacteria comprising
   a. forming a spray dryer feed comprising the gram negative bacteria; and
   b. spray drying the spray dryer feed to form a primary spray dried powder,
   wherein the spray drying of step (b) is performed under conditions such that the primary spray dried powder retains the biological activity of interest of the gram-negative bacteria and comprises at least $10^5$ CFU/gram of said gram-negative bacteria.

10. The method of embodiment 9, wherein said primary spray dried powder comprises at least $10^5$ CFU/gram to about $10^{12}$ CFU/gram.

11. The method of embodiment 9 or 10, wherein said composition comprising the spray dryer feed comprises a non-polymeric and a non-oil formulation.

12. The method of any one of embodiments 9, 10, or 11, wherein the viability of the gram-negative bacteria in the primary spray dried powder does not reduce by more than 10 fold when stored for at least 1 month at 25 degree C.

13. The method of any one of embodiments 9-12, wherein the gram-negative bacteria is a *Pseudomonas*.

14. The method of embodiment 13, wherein the gram-negative bacteria was deposited as NRRL No. B-50897.

15. The method of any one of embodiments 9-14, wherein the spray dryer feed comprises glycerol.

16. The method of any one of embodiments 9-14, wherein the spray dryer feed comprises maltodextrin.

17. A spray dryer feed comprising about 10% to about 25% dry solid cell paste.

18. The spray dryer feed of embodiment 17, wherein the spray dryer feed comprises about 10% to about 25%, about 11% to about 25%, about 12% to about 25%, about 13% to about 25%, about 14% to about 25%, about 15% to about 25%, about 16% to about 25%, about 17% to about 25%, about 18% to about 25%, about 19% to about 25%, about 20% to about 25%, about 21% to about 25%, about 22% to about 25%, about 23% to about 25% or about 24% to about 25% dry solid cell paste.

19. The spray dryer feed of embodiment 17 or 18 wherein the spray drier feed comprises about 10% to about 15%, about 11% to about 15%, about 12% to about 15%, about 13% to about 15%, about 14% to about 15%, about 10% to about 20%, about 11% to about 20%, about 12% to about 20%, about 13% to about 20%, about 14% to about 20%, about 15% to about 20%, about 16% to about 20%, about 17% to about 20%, about 18% to about 20% or about 19% to about 20% dry solid cell paste.

20. The spray dryer feed of embodiment 17, 18 or 19, wherein the spray dryer feed comprises about 13% to about 24%, about 13% to about 23%, about 13% to about 22%, about 13% to about 21%, about 13% to about 20%, about 13% to about 19%, about 13% to about 18%, about 13% to about 17%, about 13% to about 16%, about 13% to about 15%, or about 13% to about 14% dry solid cell paste.

21. A spray dryer feed comprising about 15% to about 40% dry solids.

22. The spray dryer feed of embodiment 21, wherein the spray dryer feed comprises about 15% to about 40% dry solids, about 15% to about 35% dry solids, about 15% to about 30% dry solids, about 15% to about 25% dry solids, about 15% to about 20% dry solids, about 20% to about 40% dry solids, about 20% to about 35% dry solids, about 20% to about 30% dry solids, about 20% to about 25% dry solids, about 25% to about 40% dry solids, about 25% to about 35% dry solids, about 25% to about 30% dry solids, about 30% to about 40% dry solids, about 30% to about 35% dry solids, about 30% to about 33% dry solids, about 31% to about 40% dry solids, about 32% to about 39% dry solids, about 33% to about 38% dry solids, about 34% to about 37% dry solids, about 35% to about 40% dry solids, about 36% to about 40% dry solids, about 37% to about 40% dry solids, or about 38% to about 40% dry solids.

23. The spray dryer feed of embodiment 21 or 22, wherein the about 15% to about 40% dry solids comprises about 10% to about 25% dry solid cell paste.

24. The spray dyer feed of embodiment 23, wherein the spray dryer feed comprises about 10% to about 25%, about 11% to about 25%, about 12% to about 25%, about 13% to about 25%, about 14% to about 25%, about 15% to about 25%, about 16% to about 25%, about 17% to about 25%, about 18% to about 25%, about 19% to about 25%, about 20% to about 25%, about 21% to about 25%, about 22% to about 25%, about 23% to about 25%, about 24% to about 25%, about 10% to about 15%, about 11% to about 15%, about 12% to about 15%, about 13% to about 15%, about 14% to about 15%, about 10% to about 20%, about 11% to about 20%, about 12% to about 20%, about 13% to about 20%, about 14% to about 20%, about 15% to about 20%, about 16% to about 20%, about 17% to about 20%, about 18% to about 20%, about 19% to about 20% dry solid cell paste, about 13% to about 24%, about 13% to about 23%, about 13% to about 22%, about 13% to about 21%, about 13% to about 20%, about 13% to about 19%, about 13% to about 18%, about 13% to about 17%, about 13% to about 16%, about 13% to about 15%, or about 13% to about 14% dry solid cell paste.

25. The spray dryer feed of embodiment 21 22, 23, or 24 wherein the feed comprises about 10% to about 25% dry solid cell paste, and maltodextrin.

26. The spray dryer feed of embodiment 25, wherein the amount of maltodextrin added to the cell paste is about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more by weight (weight/weight %) of the cell paste mixture (based on the assumption that the cell paste will contain about 10% to about 25% dry solids).

27. The spray dryer feed of embodiment 25 or 26, wherein the amount of maltodextrin comprises about 3% to about 7% by weight (weight/weight %) of the cell paste mixture (based on the assumption that the cell paste will contain about 10% to about 25% dry solids), about 4% to about 6% by weight (weight/weight %) of the cell paste mixture (based on the assumption that the cell paste will contain about 10% to about 25% dry solids), about 3% to about 12% by weight (weight/weight %) of the cell paste mixture (based on the assumption that the cell paste will contain 25% solids), about 8% to about 12% by weight (weight/weight %) of the cell paste mixture (based on the assumption that the cell paste will contain about 10% to about 25% dry solids), about 9% to about 11% by weight (weight/weight %) of the cell paste mixture (based on the assumption that the cell paste will contain 25% solids), by weight (weight/weight %) about 5% to about 10% of the cell paste mixture (based on the assumption that the cell paste will contain about 10% to about 25% dry solids), about 10% to about 20% of the cell paste mixture (based on the assumption that the cell paste will contain about 10% to about 25% dry solids), about 20% to about 30% of the cell paste mixture (based on the assumption that the cell paste will contain about 10% to about 25% dry solids) or about 30% to about 40% of the cell paste mixture (based on the assumption that the cell paste will contain about 10% to about 25% dry solids).

28. A formulation comprising a spray dried gram-negative bacteria composition, wherein the spray dried gram-negative bacteria composition retains the biological activity of interest of the gram-negative bacteria and said spray dried formulation comprises at least 10' CFU/gram of said gram-negative bacteria obtained by the method comprising:
    a. forming a spray dryer feed comprising the gram negative bacteria; and
    b. spray drying the spray dryer feed to form a primary spray dried powder,
wherein the spray drying of step (b) is performed under conditions such that the primary spray dried powder retains the biological activity of interest of the gram-negative bacteria and comprises at least $10^5$ CFU/gram of said gram-negative bacteria.

EXAMPLES

Example 1

A cell paste was generated from NRRL No. B-50897 and dewatered typically by centrifugation. The cell paste was assumed to have 25% dry solids. 5% by weight of glycerol was added to the cell pellet and mixed. The viscosity of the cell pellet/glycerol mixture was sufficiently reduced to allow efficient spray drying through the addition of water (usually 1-2 parts water to 1 part cell mixture).

The spray dryer feed was fed into the spray dryer nozzle via a peristaltic pump. Lab studies were conducted using a Buchi B-290 spray dryer. Spray dryer parameters are pump speed, atomization pressure, inlet temperature, and aspirator air flow %. Most experiments were run using the following settings: Atomization pressure (Q-flow): 35 mm; Inlet temperature: 115° C.; Aspirator air flow %: 100, Pump speed: 30%.

The primary spray dried powder was collected. Table 1 summarizes the primary powder following spray drying.

TABLE 1

| Ingredient | % w/w |
|---|---|
| NRRL No. B-50897 | 83.3 |
| Glycerol | 16.7 |

Example 2

A cell paste was generated from NRRL No. B-50897 and was dewatered typically by centrifugation. The cell paste was assumed to have 25% dry solids. 2.5% by weight of glycerol was added to the cell pellet and mixed. The viscosity of the cell pellet/glycerol mixture was sufficiently reduced to allow efficient spray drying through the addition of water (usually 1-2 parts water to 1 part cell mixture).

The spray dryer feed was fed into the spray dryer nozzle via a peristaltic pump. Lab studies were conducted using a Buchi B-290 spray dryer. Spray dryer parameters are pump speed, atomization pressure, inlet temperature, and aspirator air flow %. Most experiments were run using the following settings: Atomization pressure (Q-flow): 35 mm; Inlet temperature: 115 C; Aspirator air flow %: 100; Pump speed: 30%.

The primary spray dried powder was collected. Table 2 summarizes the primary powder following spray drying.

TABLE 2

| Ingredient | % w/w | Max (+10%) | Min (−10%) |
|---|---|---|---|
| NRRL No. B-50897 | 90.9 | 55.0 | 45.0 |
| Glycerol | 9.1 | 5.5 | 4.5 |

Example 3

A cell paste was generated from NRRL No. B-50897 and was dewatered typically by centrifugation. The cell paste was assumed to have 25% dry solids. 5% by weight of glycerol was added to the cell pellet and mixed. The viscosity of the cell pellet/glycerol mixture was sufficiently reduced to allow efficient spray drying through the addition of water (usually 1-2 parts water to 1 part cell mixture).

Additional carriers may be added to the mixture prior to spray drying to enhance cell survival. These carriers are typically sugars or sugar derivatives, including lactose, maltodextrin, or corn starch. The amount of carrier added can vary but a typical amount is 5% based on starting cell pellet weight. In this instance, lactose and maltodextrin were used.

The spray dryer feed was fed into the spray dryer nozzle via a peristaltic pump. Lab studies were conducted using a Buchi B-290 spray dryer. Spray dryer parameters are pump speed, atomization pressure, inlet temperature, and aspirator air flow %. Most experiments were run using the following settings: Atomization pressure (Q-flow): 35 mm; Inlet temperature: 115° C. Aspirator air flow %: 100; Pump speed: 30%.

The primary spray dried powder was collected. Tables 3 and 4 summarize the primary spray dried powder.

TABLE 3

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| Lactose | 40.0 | 44.0 | 36.0 |

TABLE 4

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| Maltodextrin | 40.0 | 44.0 | 36.0 |

Example 4

A cell paste is generated from NRRL No. B-50897 is dewatered typically by centrifugation. The cell paste is assumed to have 25% dry solids. 5% by weight of glycerol is added to the cell pellet and mixed. The viscosity of the cell pellet/glycerol mixture is sufficiently reduced to allow efficient spray drying, for example, through the addition of water (usually 1-2 parts water to 1 part cell mixture). Sodium lignosulfonate, at 5% by weight of cell pellet is added to enhance dispersibility and/or wettability following spray drying.

Additional carriers may be added to the mixture prior to spray drying to enhance cell survival. These carriers are typically sugars or sugar derivatives, including lactose, maltodextrin, or corn starch. The amount of carrier added can vary but a typical amount is 5% based on starting cell pellet weight.

The spray dryer feed is fed into the spray dryer nozzle via a peristaltic pump. Lab studies were conducted using a Buchi B-290 spray dryer. Spray dryer parameters are pump speed, atomization pressure, inlet temperature, and aspirator air flow %. Most experiments were run using the following settings: Atomization pressure (Q-flow): 35 mm; Inlet temperature: 115° C.; Aspirator air flow %: 100; Pump speed: 30%.

The spray dried powder is collected.

Example 5

A cell paste generated from NRRL No. B-50897 was dewatered typically by centrifugation. The cell paste was assumed to have 25% dry solids. 5% by weight of glycerol was added to the cell pellet and mixed. The viscosity of the cell pellet/glycerol mixture is sufficiently reduced to allow efficient spray drying, for example, through the addition of water (usually 1-2 parts water to 1 part cell mixture). Sodium lignosulfonate, at 5% by weight of cell pellet is added to enhance dispersibility and/or wettability following spray drying.

Additional carriers may be added to the mixture prior to spray drying to enhance cell survival. These carriers are typically sugars or sugar derivatives, including lactose, maltodextrin, or corn starch. The amount of carrier added can vary but a typical amount is 5% based on starting cell pellet weight.

The spray dryer feed is fed into the spray dryer nozzle via a peristaltic pump. Lab studies were conducted using a Buchi B-290 spray dryer. Spray dryer parameters are pump speed, atomization pressure, inlet temperature, and aspirator air flow %. Most experiments were run using the following settings: Atomization pressure (Q-flow): 35 mm; Inlet temperature: 115 C; Aspirator air flow %: 100; Pump speed: 30%.

The spray dried powder is collected.

In specific embodiments, additional ingredients are blended into the spray dried powder until well mixed. This can include the remainder of the carrier if it was not all added during the spray drying process. Additional ingredients include flow aids such as calcium silicates at 1-10% by weight and additional dispersants. Such additional ingredients include, but are not limited to one or more of the following: sugars, including but not limited to, lactose, dextrose, sucrose, milk powders, whey protein, casein, maltodextrin; mineral carriers, including but not limited to, all types of clays (bentonite, montmorillonite, kaolin, hectorite etc.), silicas, diatomaceous earths, perlite, zeolite, carboxymethyl cellulose, starches (potato, rice, corn, tapioca, etc.), flours: protectants, including but not limited to, glycerol, sorbitol, xanthan gum, duitan gum, gum arabic, sodium alginate, gelatin, trehalose, fructo- and galacto-oligosaccharides, mannitol, dextran, yeast extract, dextrin, pectin: lignosulfonates, Polyvinyl pyrrolidone, alcohol ethoxylates, organosilicone surfactants, polyglycerol fatty esters, sorbitan fatty acid ethoxylates, siloxanes, acrylates, alkyl naphthalene sulfonate condensates, anionic comb polymers, block copolymers, diester sulfosuccinates, phosphate esters, tristyrylphenol ethoxylates, alkyl benzene sulfonates, castor oil ethoxylate, vegetable oils (ethoxylated and methylated varieties as well), sulfosuccinates, ethyl lactates, alkylamine ethoxylates, diester sulfosuccinates, dioctyl sodium sulfosuccinate, ethoxylated acetylenic diol, sodium lauryl sulfate, salts, proteins, peptides and amino acids.

Tables 5-17 provides examples of the final spray dried powder formulation.

TABLE 5

(App 3)

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| *Sipernat 22S | 40.0 | 44.0 | 36.0 |

*equivalents include, but are not limited to, Sipernat 22, Sident 22S, Sipernat 50, Sipernat 50S, HI-SIL 233 Silica, and HI-SIL SAC Silica.

TABLE 6

(App 3)

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| Lactose | 35.0 | 38.5 | 31.5 |
| *Sipernat 22S | 5.0 | 5.5 | 4.5 |

*equivalents include, but are not limited to, Sipernat 22, Sident 22S, Sipernat 50, Sipernat 50S, HI-SIL 233 Silica, and HI-SIL SAC Silica.

TABLE 7

(App 3)

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| Maltodextrin | 35.0 | 38.5 | 31.5 |
| *Sipernat 22S | 5.0 | 5.5 | 4.5 |

*equivalents include, but are not limited to, Sipernat 22, Sident 22S, Sipernat 50, Sipernat 50S, HI-SIL 233 Silica, and HI-SIL SAC Silica.

TABLE 8

(App 3)

| Ingredient | CAS No | % w/w | Max (+10%) | Min (−10%) |
|---|---|---|---|---|
| NRRL No. B-50897 | N/A | 50.0 | 55.0 | 45.0 |
| Glycerol | 56-81-5 | 10.0 | 11.0 | 9.0 |
| Maltodextrin | 9050-36-6 | 30.0 | 33.0 | 27.0 |
| *Sipernat 22S | 112926-00-8 | 10.0 | 11.0 | 9.0 |

*equivalents include, but are not limited to, Sipernat 22, Sident 22S, Sipernat 50, Sipernat 50S, HI-SIL 233 Silica, and HI-SIL SAC Silica.

TABLE 9

(App 3)

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |

TABLE 9-continued (App 3)

| Ingredient | % w/w | Max (+10%) | Min (−10%) |
|---|---|---|---|
| Lactose | 30.0 | 33.0 | 27.0 |
| *Sipernat 22S | 10.0 | 11.0 | 9.0 |

*equivalents include, but are not limited to, Sipernat 22, Sident 22S, Sipernat 50, Sipernat 50S, HI-SIL 233 Silica, and HI-SIL SAC Silica.

TABLE 10

(App 3)

| Ingredient | % w/w | Max (+10%) | Min (−10%) |
|---|---|---|---|
| NRRL No. B-50897 | 50.0 | 55.0 | 45.0 |
| Glycerol | 5.0 | 5.5 | 4.5 |
| Maltodextrin | 35.0 | 38.5 | 31.5 |
| *Sipernat 22S | 10.0 | 11.0 | 9.0 |

*equivalents include, but are not limited to, Sipernat 22, Sident 22S, Sipernat 50, Sipernat 50S, HI-SIL 233 Silica, and HI-SIL SAC Silica.

TABLE 11

(App 3)

| Ingredient | % w/w | Max (+10%) | Min (−10%) |
|---|---|---|---|
| NRRL No. B-50897 | 50.0 | 55.0 | 45.0 |
| Glycerol | 5.0 | 5.5 | 4.5 |
| Lactose | 35.0 | 38.5 | 31.5 |
| *Sipernat 22S | 10.0 | 11.0 | 9.0 |

*equivalents include, but are not limited to, Sipernat 22, Sident 22S, Sipernat 50, Sipernat 50S, HI-SIL 233 Silica, and HI-SIL SAC Silica.

TABLE 12

App3

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| *Silwet 408 | 2.0 | 2.2 | 1.8 |
| Lactose | 30.0 | 33.0 | 27.0 |
| **Sipernat 22S | 8.0 | 8.8 | 7.2 |

*equivalents include various surfactants, including but are not limited to, as Xiameter OFX- 5211 Fluid, Q-5212 Super Wetting Agent, and Break-Thru S 200.
**equivalents include, but are not limited to, Sipernat 22, Sident 22S, Sipernat 50, Sipernat 50S, HI-SIL 233 Silica, and HI-SIL SAC Silica.

TABLE 13

App3

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| *Silwet 408 | 2.0 | 2.2 | 1.8 |
| Maltodextrin | 30.0 | 33.0 | 27.0 |
| **Sipernat 22S | 8.0 | 8.8 | 7.2 |

*equivalents include various surfactants, including but are not limited to, as Xiameter OFX- 5211 Fluid, Q-5212 Super Wetting Agent, and Break-Thru S 200.
**equivalents include, but are not limited to, Sipernat 22, Sident 22S, Sipernat 50, Sipernat 50S, HI-SIL 233 Silica, and HI-SIL SAC Silica.

TABLE 14

App3

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| *Marasperse AG | 10.0 | 11.0 | 9.0 |
| Lactose | 20.0 | 22.0 | 18.0 |
| **Sipernat 22S | 10.0 | 11.0 | 9.0 |

*equivalents include, but are not limited to, Polyfon F, Polyfon T, Polyfon O, Polyfon H, Marasperse N-22, Vanisperse CB, Ultrazine NA, Ufoxane 3A, Borresperse NA, Borresperse 3A, and Kraftsperse EDF-450
**equivalents include, but are not limited to, Sipernat 22, Sident 22S, Sipernat 50, Sipernat 50S, HI-SIL 233 Silica, and HI-SIL SAC Silica.

TABLE 15

App3

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| *Marasperse AG | 10.0 | 11.0 | 9.0 |
| Maltodextrin | 20.0 | 22.0 | 18.0 |
| **Sipernat 22S | 10.0 | 11.0 | 9.0 |

*equivalents include, but are not limited to, Polyfon F, Polyfon T, Polyfon O, Polyfon H, Marasperse N-22, Vanisperse CB, Ultrazine NA, Ufoxane 3A, Borresperse NA, Borresperse 3A, and Kraftsperse EDF-450
**equivalents include, but are not limited to, Sipernat 22, Sident 22S, Sipernat 50, Sipernat 50S, HI-SIL 233 Silica, and HI-SIL SAC Silica.

TABLE 16

App3

| Ingredient | % w/w | Max (+10%) | Min (−10%) |
|---|---|---|---|
| NRRL No. B-50897 | 50.0 | 55.0 | 45.0 |
| Glycerol | 10.0 | 11.0 | 9.0 |
| *Marasperse AG | 10.0 | 11.0 | 9.0 |
| ***Silwet 408 | 2.0 | 2.2 | 1.8 |
| Lactose | 20.0 | 22.0 | 18.0 |
| **Sipernat 22S | 8.0 | 8.8 | 7.2 |

*equivalents include, but are not limited to, Polyfon F, Polyfon T, Polyfon O, Polyfon H, Marasperse N-22, Vanisperse CB, Ultrazine NA, Ufoxane 3A, Borresperse NA, Borresperse 3A, and Kraftsperse EDF-450
**equivalents include, but are not limited to, Sipernat 22, Sident 22S, Sipernat 50, Sipernat 50S, HI-SIL 233 Silica, and HI-SIL SAC Silica.
***equivalents include, but are not limited to, Xiameter OFX-5211 Fluid, Q-5212 Super Wetting Agent, and Break-Thru S 200.

TABLE 17

App3

| Ingredient | % w/w | Max (+10%) | Min (−10%) |
|---|---|---|---|
| NRRL- B-50897 | 50.0 | 55.0 | 45.0 |
| Glycerol | 10.0 | 11.0 | 9.0 |
| *Marasperse AG | 10.0 | 11.0 | 9.0 |
| ***Silwet 408 | 2.0 | 2.2 | 1.8 |
| Maltodextrin | 20.0 | 22.0 | 18.0 |
| **Sipernat 22S | 8.0 | 8.8 | 7.2 |

*equivalents include, but are not limited to, Polyfon F, Polyfon T, Polyfon O, Polyfon H, Marasperse N-22, Vanisperse CB, Ultrazine NA, Ufoxane 3A, Borresperse NA, Borresperse 3A, and Kraftsperse EDF-450
**equivalents include, but are not limited to, Sipernat 22, Sident 22S, Sipernat 50, Sipernat 50S, HI-SIL 233 Silica, and HI-SIL SAC Silica.
***equivalents include, but are not limited to, Xiameter OFX-5211 Fluid, Q-5212 Super Wetting Agent, and Break-Thru S 200.

Example 6. Pilot Spray Dryer Procedure

Spray drying was performed in a SPX PSD 52 pilot spray dryer equipped with a two fluid nozzle. NRRL No. B-50897 cell broth was fermented and centrifuged to concentrate the broth to dry cell solids of ~17% as measured on a heated moisture balance.

Several cell concentrate batches were formulated in preparation for spray drying as follows: Each sample contained 7 kg cell concentrate. Glycerol was added at 20% of the total cell solids in the concentrate and mixed thoroughly. Various spray aids were added to the cell concentrate/glycerol samples and mixed until homogeneous. These spray aids include maltodextrin DE 10, maltodextrin DE 18, and lactose at 20% and 60% of the cell solids. Additionally, the above samples with spray aids at the 20% level were also prepared with the lignosulfonate Marasperse AG at 20% of the cell solids.

Spray drying was performed at an inlet temperature of 150° C. and outlet temperatures of 50° C.-80° C. and an atomization pressure of 80-105 psi on the air stream of the two fluid nozzle. The formulated cell feed slurries were pumped into the spray dryer using a peristaltic pump #1395 with an operating flow rate from 2-9 L/hr and size 16 silicone tubing. An outlet temperature of 80 C gave an acceptable water activity of the product at ~0.2. Spray drying was also performed at inlet temperatures from 175° C.-200° C. and outlet temperatures up to 95° C. Dried powder (~1-3 kg per sample depending on feed composition and spray drying conditions) was collected through the attached cyclone into a collection pot.

Viable cells in the range of 1e7 cfu/g were recovered when using an inlet/outlet temperature of 150° C./80° C., 80 psi air pressure, and glycerol and maltodextrin DE 10 at 20% and 60% wt. of the cell solids, respectively.

Example 7. Spray Dryer Procedure for Gram Negative Bacteria

NRRL No. B-50897 cell broth are fermented and centrifuged to concentrate the broth to dry cell solids of ~17% as measured on a heated moisture balance. Cell concentrate batches are formulated in preparation for spray drying as follows. Feed slurry comprising NRRL No. B-50897 cell concentrate (~20% dry cell solids) and maltodextrin at 5-40%, 5-10%. 10-15%, 15%-20%, 20-25%, 25%-30%, 30%-35%, 35%-40%, or 40%-45% based on dry cell solids weight. No glycerol is added to the spray dry feed.

The spray dry feed is fed into a commercial spray drying tower with a short residence time (6 s) and a two fluid nozzle to minimize shear on feed. A low pump feed and spray gas pressure (<500 psi) is employed. Inlet air temperature is about 150° C. and outlet temperature is about 80° C. or lower. The dried particle size is in the range of 50-200 um. Immediate discharge of material from cyclone away from heat or directly into fluidized bed dryer to further cool the product and/or agglomerate it occurs.

What is claimed is:

1. A method for producing a spray dried formulation comprising a gram-negative bacteria comprising
    a. forming a spray dryer feed comprising the gram negative bacteria, wherein the spray dryer feed comprises a cell paste mixture; and
    b. spray drying the spray dryer feed in a spray dryer comprising a heated tower thereby forming a primary spray dried powder,
   wherein the spray drying of step (b) comprises introducing said spray dryer feed into the spray dryer using an inlet temperature of 170° C. to 200° C., and
   wherein the primary spray dried powder emitted from the spray dryer retains the biological activity of interest of the gram-negative bacteria and comprises about $10^5$ CFU/gram to about $10^{12}$ CFU/gram of said gram-negative bacteria.

2. The method of claim 1, wherein the residence time in the tower is about 6 seconds.

3. The method of claim 2, wherein the spray dryer feed further comprises maltodextrin.

4. The method of claim 3, wherein the maltodextrin is present in an amount of about 10% to about 20% of the cell paste mixture.

5. The method of claim 1, wherein the spray dryer feed comprises a non-polymeric and a non-oil formulation.

6. The method of claim 1, wherein the viability of the gram-negative bacteria in the primary spray dried powder does not reduce by more than 10-fold when stored for about 1 month at 25 degrees C.

7. The method of claim 1, wherein the gram-negative bacteria is a *Pseudomonas* bacteria.

8. The method of claim 7, wherein the gram-negative bacteria is the bacterial strain deposited as NRRL No. B-50897.

9. The method of claim 1, wherein the spray dryer feed comprises glycerol.

10. The method of claim 1, wherein the spray dryer feed comprises maltodextrin.

11. The method of claim 1, wherein the spray dried gram-negative bacteria composition is spray dried using an outlet temperature of 60° C. to 100° C.

* * * * *